United States Patent [19]

Colby, Jr. et al.

[11] 4,262,090

[45] Apr. 14, 1981

[54] INTERFERON PRODUCTION

[75] Inventors: Clarence Colby, Jr., Carmel Valley, Calif.; Dan W. Denney, Jr., Lebanon, Tenn.

[73] Assignee: Cetus Corporation, Berkeley, Calif.

[21] Appl. No.: 45,031

[22] Filed: Jun. 4, 1979

[51] Int. Cl.³ .............................................. C12P 19/34
[52] U.S. Cl. ....................................... 435/91; 435/68; 435/172; 435/5; 435/240; 435/811; 424/85
[58] Field of Search ............................ 435/92, 91, 811

[56] References Cited

U.S. PATENT DOCUMENTS 3,773,924  11/1973  Ho et al. ............................... 435/811

OTHER PUBLICATIONS

Jarvis et al., Somatic Cell Genetics, vol. 4, No. 6, pp. 677-697 (1978).
King, Handbook of Genetics, vol. 5, pp. 267-289 (1976).

*Primary Examiner*—Alvin E. Tanenholtz
*Attorney, Agent, or Firm*—Bertram I. Rowland

[57] ABSTRACT

Method for preparing interferon, mRNA for interferon, and competent recombinant DNA containing dsDNA and cDNA from mRNA coding for mammalian interferon. The method employs crossing a mutant mammalian cell which is semiconstitutive for interferon with a cell derived from the same or different mammal having wild type gene(s) for interferon and for the regulation of interferon synthesis and desirably having phenotypic properties allowing for selection of the hybrid cells. The desired hybrid clones are then induced to produce IF mRNA, wherein the amounts of mRNA for interferon are greatly enhanced over the amounts normally obtained from wild type cell strains. The mRNA is employed to produce cDNA which codes for the mammalian interferon. The single stranded cDNA is employed as a template to prepare dsDNA which is then combined with a replicon recognized by a microorganism host to provide a recombinant DNA. The microorganism host is transformed with the recombinant DNA, so as to provide a source for the interferon gene, as well as interferon.

5 Claims, No Drawings

INTERFERON PRODUCTION

BACKGROUND OF THE INVENTION

1. Field of the Invention

Interferon is a glycoprotein whose synthesis is induced in cultured cells principally by viruses or by natural or synthetic double stranded RNAs. This induction requires de novo macromolecular synthesis as indicated by its sensitivity to inhibitors of both RNA and protein synthesis. interferon is believed to be secreted by the induced cell, whereby the secreted interferon interacts with other cells resulting in the establishment, maintenance and expression of an intracellular antiviral state.

The amount of interferon which is produced is exquisitely small, so that its isolation has been extremely elusive. The primary source of human interferon is from Helsinki, Finland, where partially purified human leukocyte interferon is obtained from blood given by blood donors. Because of the limited source of interferon, and the difficulties in purification and concentration, the cost of interferon is prohibitively high. In view of its antiviral nature and its acceptability by a mammalian host, the production of interferon in useful amounts holds great promise for its use in treatment of a wide variety of viral induced disorders or malignancies.

2. Description of the Prior Art

U.S. Pat. No. 3,699,222 teaches the production of interferon by induction of monolayer cell cultures with virus. Jarvis and Colby, Cell 14, 355 (1978) disclose the isolation and characterization of a mutant 3T6 cell engaged in the semiconstitutive synthesis of interferon. Jarvis, et al. Somatic Cell Genetics 4, 677 (1978) disclose the hybridization of murine cells with expression of a dominant mutation affecting the regulation of interferon production.

SUMMARY OF THE INVENTION

Method and compositions for producing mammalian interferon are provided. The method comprises inducing mutagenesis in a mammalian cell to provide semiconstitutive synthesis of mammalian interferon; hybridizing the mutant cell either intra- or interspecifically with a cell having a wild type gene(s) for interferon synthesis and its regulation and desirably having one or more phenotypic markers for hybrid selection, and inducing interferon and IF mRNA production by viruses or dsRNA and obtaining mRNA specific for interferon. cDNA is prepared from the mRNA, which is then used as a template to make dsDNA and the dsDNA combined with a replicon recognized by a microorganism host to provide a functional recombinant DNA which is used for transformation of the host. Upon growth of the host, the host may be used as a source for interferon, as well as additional IF genes and IF gene containing plasmids.

DESCRIPTION OF THE SPECIFIC EMBODIMENTS

In accordance with the subject invention, novel methods and compositions are provided for producing significant amounts of mRNA which codes for mammalian interferon (IF mRNA). By employing recombinant DNA technology, the mRNA can be used to produce interferon, the interferon gene, and IF dsDNA containing recombinant DNA. Prior to the subject invention, in view of the extremely small amounts of interferon that are produced by virus induced cells and as a concomitant, even smaller amounts of mRNA, it has not been feasible to employ recombinant DNA technology to produce interferon. By virtue of the subject invention, cell cultures can be produced which provide useful amounts of mRNA, so as to allow for the first time the production of the interferon gene for incorporation into recombinant DNA and transformation of microorganisms.

The subject invention is predicated upon the ability to mutate and isolate a mammalian cell which is semiconstitutive in its production of interferon. What this intends, is that the cell continuously produces interferon at low level. In effect, the regulatory system which supresses the production of interferon except when induced by viruses or dsRNA, has been at least partially inactivated so that the interferon gene is continuously transcribed to produce mRNA, which is then translated to interferon.

The mutant cell is hybridized with an inter- or intra-specific cell having a wild type IF operon for IF synthesis and regulation, and desirably one or more phenotypic markers to allow for selection of hybrid cells. Upon induction of interferon production by employing viruses or double-stranded RNA, it is found that the hybrid cell produces substantially greater amounts of IF mRNA and interferon than is normally produced by either the original mutant cell or the wild type cell. By harvesting mRNA which is enriched for IF mRNA, cDNA may be produced by conventional means, followed by the production of double-stranded DNA (dsDNA) from the cDNA. The dsDNA may then be used to form a recombinant DNA with a replicon compatible with a microorganism host to provide for production of the interferon gene, interferon, and recombinant DNA containing the IF gene.

A number of steps are required in accordance with the subject process. Each step will be considered independently, since it can be performed independent of the previous steps, so long as one has produced the appropriate materials by any convenient means. The following is a list of the involved steps.

1. mutagenesis, selection and screening of a mammalian cell semiconstitutive for IF production (IF$^{sc}$).
2. hydridization of the mutant cell with a mammalian cell having a wild type IF gene and optionally one or more phenotypic properties for selection.
3. inducing IF mRNA production with dsRNA, or with certain viruses, and isolation of mRNA;
4. preparation of IF cDNA from IF mRNA and of IF dsDNA from IF cDNA.
5. joining IF dsDNA with a replicon recognized by a microorganism host to form a functional recombinant DNA and transforming said host with said recombinant DNA.
6. cloning said transformed host to replicate the IF dsDNA and produce interferon and isolating the interferon as a concentrate.

Mutagenesis and Selection

Mutagen-sensitive mammalian cells may be chosen having appropriate phenotypic markers for selection of the ultimate hybrid cell. The cells may then be subjected to mutagenic compounds or conditions and the resulting cells screened for the semiconstitutive production of interferon. Various mutagenic materials may be used, such as nitroso compounds e.g. nitrosoguanidine, polycyclic aromatics, mustards or ultraviolet light. The techniques for inducing mutation are well known and do not require exemplification here. See Colby and Jarvis, supra.

One can select the cells having semiconstitutive interferon production by their viral resistance ($V^r$). By plating the cells on an appropriate nutrient medium and infecting the cells with viruses, surviving clones may then be screened for their interferon production ability.

A test has been developed to establish the semiconstitutive production of interferon. The level of the interferon-induced antiviral state by the semiconstitutive interferon production of an adjacent cell is determined by preparing single cell suspensions in minimal essential media supplemented by non-essential amino acids and other appropriate nutrients. The cells are seeded into shallow wells at a density such that after a reasonable period of growth, confluent monolayers are obtained. When confluent layers are obtained, conveniently about 18 hours after seeding, the medium is removed and the cultures are washed, usually twice. An appropriate virus at an MOI (multiplicity of infection) equal to about seven (a normally lethal dosage) is added in an appropriate medium, conveniently the same nutrient medium employed previously. The virus is adsorbed at 37° C. for about 30 min at the end of which period and again at 90 min post-infection, the monolayers are washed, usually twice, and fresh medium added. After a period of time equal to one replicative cycle, the medium is harvested and the virus titered by any convenient means, for example, a plaque assay. By employing substantially equal amounts of single cells of the cell suspected of semiconstitutive interferon production and cells susceptible to interferon's antiviral activity, a substantial reduction of the virus harvest is suggestive of interferon production.

To establish the presence of interferon as the causal agent, one can repeat the above described experiment, but include in the nutrient medium, a predetermined amount of anti-interferon antiserum. (By anti-interferon is intended antibodies specifically binding to the interferon produced by the mammalian cell species.) The presence of the anti-IF antiserum should inhibit the effect of secreted interferon, so that the virus titer in the presence of such antiserum should be substantially enhanced over the titer in absence of the antiserum.

Cell Fusion

After selection of the $IF^{sc}$ mutant cells, the cells are then hybridized with wild type IF cells, which are inter- or intraspecific with the mutant $IF^{sc}$ cell. The two parental somatic cells are mixed, plated, incubated, and the monolayers washed, followed by incubation in the presence of a fusing medium e.g. a concentrated solution of a polyethylene glycol of about 5,000 to 10,000 molecular weight. The incubation is for short times, generally less than about 5 min. The fusing solution is then rapidly removed, the monolayers washed and incubated in growth medium. After one to three days, the cells are trypsinized and plated at low densities in an appropriate selective medium.

Desirably, the parental cells have appropriate phenotypic markers, so that one can select for the hybrid by providing an environment which only allows for selection of the hybrid e.g. permits sustained growth of the hybrid. After cloning the cells, a plurality of generations are grown, generally from about 25 to 100, in a selective environment, so as to insure the substantially sole presence of the hybrid cell.

Semiconstitutive interferon production can then be determined in accordance with the test described previously.

IF mRNA Production

From the $IF^{sc}$ hybrids which are obtained, one identifies those hybrids which overproduce the IF as follows. The cells are infected with an appropriate virus, at MOI=1 or above. The virus employed is usually inactive or a poor replicator. Illustrative viruses include members of the paramyxovirus and reoviridiae families, the latter family including reovirus, orbivirus and rotavirus. Individual viruses include Newcastle disease virus (NDV) and blue tongue virus (BTV).

After treating the cultures in accordance with conventional techniques, the cells are collected by centrifugation, swollen on ice and ruptured. After removal of the nuclei by centrifugation, the supernatant is isolated and centrifuged, with the resulting pellet containing the membrane-bound polysomes. The pellet may be resuspended in appropriate medium, deproteinized by conventional means and the RNA precipitated by adding buffer and ethanol.

The poly A-containing mRNA may be concentrated employing chromatography on oligo dT-cellulose or poly dU-Sepharose and the process repeated for enhancing the mRNA concentration. The mRNA is then resolved by employing appropriate resolving means, such as density gradient centrifugation or gel electrophoresis and the fractions collected. The mRNA fractions may then be assayed for IF mRNA by microinjection into frog oocytes or employing the mRNA dependent reticulocyte translation system of Pelham and Jackson, Europ. J. of Biochem. 67:247(1976).

Preparation of IF cDNA, IF dsDNA and recombinant DNA

The complementary DNA may be prepared in accordance with conventional means employing reverse transcriptase (Buell, et al. J. Biol. Chem. 253:2471 (1978) particularly avian myeloblastosis virus reverse transcriptase. The double stranded DNA may then be achieved by employing DNA polymerase I and S1 nuclease in accordance with Wickens, et al. ibid., 253:2483 (1978).

Various techniques may be employed as well as various replicons to provide a recombinant DNA which will be acceptable to a microorganism host, such as bacteria, yeast, or the like. The replicon may be derived from a plasmid, virus, or chromosome, where the source of the replicon is accepted by the host organism. The dsDNA produced from the cDNA containing the gene for interferon, may be joined to the replicon by blunt-end ligation, with a T4 ligase under conventional conditions; by employing a restriction enzyme, which provides staggered cleavage, so as to produce cohesive or sticky ends, providing that the cleavage does not occur at the replicon site or within the IF gene; or one can chew back or add on to one of the ends of each of the strands, using an appropriate enzyme, so that complementary sequences are produced to provide the desired cohesive ends, e.g. employing deoxynucleotidyl transferase. The resulting recombinant DNA may then be ligated prior to transformation of the host or allowed to be ligated in the host, the former being preferable. Techniques for ligation are amply described in the literature.

After preparation of the functional recombinant DNA composition, the host organism is transformed under transforming conditions. An appropriate transforming solution is 0.1–0.5 M calcium chloride containing the host e.g. bacteria, to which is added the DNA composition and the mixture incubated at about 0°, followed by subjecting the microorganism to a heat pulse. The transformed host is then selected by the phenotypic properties of the recombinant DNA by plating and cloning with a selective medium.

The transformed cells are then cloned in a nutrient medium affording the production of interferon, concomitant with IF mRNA and the IF gene containing recombinant DNA. The secreted interferon may be purified and concentrated by conventional means, such as precipitation with ammonium sulfate, dialysis to remove salts, chromatography, gel electrophoresis, or the like. The mRNA and recombinant DNA may also be isolated by conventional means as described in the literature. The cells are monitored to maintain the cloning of the transformed strain and prevent the establishment of other mutant or revertant strains which do not have the desired properties.

Various mammalian interferons may be produced, such as murine interferon, interferon for domestic animals, e.g. equine, bovine, canine, feline, etc., and the various types of human interferon, such as human leukocyte interferon (HLeIF), human fibroblast interferon (HFIF) and human lymphoblastoid interferon (HLyIF).

The following examples are offered by way of illustration and not by way of limitation.

EXPERIMENTAL

Parental cell lines used in these experiments include: 3T6 (Jarvis and Colby (1978), Cell 6:355–363), 3T6-V$^r$B2 (ibid), and 2TGO-13 (Jaj and Ozer (1977), Genetics 86:832–833). The line 3T6-V$^r$B2 is a subclonal isolate of a mutagenized population of 3T6 cells (Morgan, et al. (1973), J. Gen. Virol. 20:377–385) possessing the phenotypic markers: resistance to virus infection (V$^r$) and semiconstitutive synthesis of interferon (IF$^{sc}$). The cell line 2TGO-13 is a derivative of Balb/3T3, possessing one codominant and two recessive markers; resistance to 3.0 mM ouabain, hypoxanthine guanine phosphoribosyltransferase deficient (HGPRT$^-$), and temperature sensitive for DNA synthesis, respectively. Two of the parental cells, 3T6 and 3T6-V$^r$B2 and all hybrid clones were grown at 37° C. in Dulbecco's modified Eagle's medium (DME) supplemented with 2 mM glutamine, 10% heat-inactivated fetal calf serum (FCS), 100 µ/ml penicillin and 100 µg/ml streptomycin. The third parental line 2TGO-13, was grown in the same medium at 34° C.

Cell fusions were performed as follows. After mixing $10^6$ cells of each parent, the mixture was plated into 60 mm dishes. After 6 hrs incubation at 37° C., the monolayers were washed 3× with DME, and 1.5 ml of a 50% (w/v) solution of PEG6,000 in DME was added. Incubation in the presence of PEG was carried out at room temperature for 20 sec in the case of 3T6 V$^r$B2×2TGO-13 fusions and 90 sec in the case of 3T6×2TGO-13 fusions. The PEG solution was removed rapidly at the end of the treatment period, the monolayers quickly washed 3× with DME and the cultures were placed at 37° C. Five minutes after washing, and again 30 min later, the medium was removed and DME-10FCS was added. The monolayers were then incubated for 18 hrs at 37° C. at which time the cells were trypsinized, counted in the presence of 0.05% trypan blue dye and plated at densities between $10^5$ and $10^3$ viable cells/100 mm dish in DME-10FCS. After 24 hrs at 37° C., the medium was removed and replaced with DME-10FCS containing 1.5 mM ouabain. The cells were also switched to 39° C. at this time. Cultures were refed at three day intervals with freshly prepared medium. Clones of presumptive hybrid cells were picked after 12–14 days from dishes originally seeded with $10^3$ cells. Frequency of colony formation was also determined at this time by staining with crystal violet. All clones were perpetuated at 39° C. in the presence of ouabain for approximately 40–50 generations before being transferred to medium without ouabain. Karyotyping was carried out as follows. Mitotic cells were collected by shaking and mild trypsinization of cultures in log-phase growth, followed by centrifugation at 1,000 g for 5 min. The cells were swollen by incubation for 20 min at 37° C. in 75 mM KCl, and again collected by centrifugation. Cells were then fixed for 10 min at room temperature using a 3:1 mixture of anhydrous methanol and glacial acetic acid. Following spreading, the metaphase smears were stained for 4 min at room temperature using a 2% solution of Geimsa stain in water. Metaphase chromosome number and constitution were determined at 1,000× magnification using an oil immersion objective.

Interferon-induced antiviral state was measured as follows. The level of the interferon-induced antiviral state was measured by the reduction of vesicular stomatitis virus (VSV) yields. Single cell suspensions in minimal essential medium supplemented with nonessential amino acids (F-15) and 10% FCS were seeded into 16 mm wells at a density such that at 37°, confluence was achieved within 18–24 hrs post-plating. The number of cells present for each cell type was then determined. After achieving confluence, the medium was removed, the cultures washed twice, followed by infection with VSV at an input multiplicity of infection (MOI) equal to 7.0. The VSV was added to each well in 0.2 ml of F15-2FCS. Virus was adsorbed at 37° C. for 30 min. At the end of this period and again 90 min post infection, the monolayers were washed twice and 1 ml of fresh F15-2FCS added. After 15 hrs at 37° C., the cultures were harvested and the yield of VSV determined. The titer of newly synthesized VSV was determined by duplicate plaque assay on BHK$_{21}$ cells. The virus titers are normalized per $10^5$ cells infected, based on the number of cells previously determined. Clones isolated from 3T6×2TGO-13 fusions and 3T6-V$^r$B2×2TGO-13 fusions are indicated as 6-2$_n$ and V$^r$-2$_n$ respectively.

TABLE 1

| | Replication of VSV by Parent and Presumptive Hybrid Clones | | |
|---|---|---|---|
| Cell Line | VSV pfu/$10^5$ Cells | Cell Line | VSV pfu/$10^5$ Cells |
| 3T6 | $1.15 \times 10^8$ | V$^r$-2$_7$ | $6.6 \times 10^5$ |
| 3T6-V$^r$B2 | $1.37 \times 10^5$ | V$^r$-2$_8$ | $4.0 \times 10^4$ |
| 2TGO-13 | $3.50 \times 10^7$ | V$^r$-2$_9$ | $3.6 \times 10^5$ |
| 6-2$_1$ | $1.1 \times 10^7$ | V$^r$-2$_{10}$ | $1.3 \times 10^3$ |
| 6-2$_2$ | $1.4 \times 10^7$ | V$^r$-2$_{11}$ | $2.7 \times 10^3$ |
| 6-2$_3$ | $1.1 \times 10^7$ | V$^r$-2$_{12}$ | $9.2 \times 10^4$ |
| 6-2$_4$ | $1.6 \times 10^7$ | V$^r$-2$_{13}$ | $1.1 \times 10^5$ |
| 6-2$_5$ | $3.9 \times 10^7$ | V$^r$-2$_{14}$ | $2.0 \times 10^7$ |
| 6-2$_6$ | $5.6 \times 10^7$ | V$^r$-2$_{15}$ | $7.5 \times 10^2$ |
| 6-2$_7$ | $1.7 \times 10^7$ | V$^r$-2$_{16}$ | $9.5 \times 10^4$ |
| V$^r$-2$_1$ | $8.1 \times 10^4$ | V$^r$-2$_{17}$ | $7.2 \times 10^4$ |
| V$^r$-2$_2$ | $6.3 \times 10^4$ | V$^r$-2$_{18}$ | $1.6 \times 10^3$ |
| V$^r$-2$_3$ | $5.9 \times 10^3$ | V$^r$-2$_{19}$ | $2.7 \times 10^4$ |
| V$^r$-2$_4$ | $1.05 \times 10^4$ | V$^r$-2$_{20}$ | $3.6 \times 10^3$ |

TABLE 1-continued

Replication of VSV by Parent and Presumptive Hybrid Clones

| Cell Line | VSV pfu/$10^5$ Cells | Cell Line | VSV pfu/$10^5$ Cells |
|---|---|---|---|
| $V^r$-$2_5$ | $1.7 \times 10^4$ | $V^r$-$2_{21}$ | $8.6 \times 10^6$ |
| $V^r$-$2_6$ | $2.6 \times 10^4$ | $V^r$-$2_{21}$ | $8.6 \times 10^6$ |

Of the clones identified in Table 1, one from the 3T6×2TGO-13 fusions and six from the 3T6-$V^r$B2×2TGO-13 fusions were investigated further. After karyotyping, based on the metacentric chromosome number and prototrophic properties, it was decided that the colonies chosen were syncaryons. In order to demonstrate that interferon induced an antiviral state in virus susceptible cells, co-cultivation was carried out with the hybrids prepared as described above and mouse $L_{929}$ cells. The co-cultivation was performed by combining equal numbers ($6 \times 10^4$) of the appropriate cells (parental or hybrid) with $L_{929}$ cells and the mixture plated into 16 mm wells in a final volume of 1 ml of F15-10FCS, either in the presence of or the absence of 3.2 NU/ml of antiserum (see Jarvis & Colby, supra; and Gresser, et al. (1976) J. Expl. Med. 144 1305–1315). The cultures were incubated for 24 hrs at 37° C., at which time all cultures had reach confluency. At this time representatives of each mixed culture were trypsinized and the total number of cells was determined. Based on this number, the cultures were infected with VSV using an input MOI equal to 7.0 and the yield of infectious virus produced 10 hrs post infection determined.

The following table indicates the results.

TABLE 2

Detection of an Interferon-Induced Antiviral State in $L_{929}$ Cells

| Cell Mixture | Antiserum | $Log_{10}$ VSV Yield$^a$ | $Log_{10}$ VSV yield Reduction$^b$ |
|---|---|---|---|
| 2TGO-13/$L_{929}$ | − | 7.51 | −0.22 |
| 3T6/$L_{929}$ | − | 8.46 | −0.58 |
| 3T6-$V^r$B2/$L_{929}$ | − | 4.85 | 2.22 |
|  | + | 6.98 | 0.09 |
| 6-$2_1$/$L_{929}$ | − | 7.79 | −0.28 |
|  | + | 7.65 | −0.15 |
| $V^r$-2/$L_{929}$ | − | 5.75 | 1.32 |
|  | + | 7.36 | −0.29 |
| $V^r$-$2_{10}$/$L_{929}$ | − | 3.29 | 3.78 |
|  | + | 6.94 | 0.13 |
| $V^r$-$2_{15}$/$L_{929}$ | − | 4.29 | 2.87 |
|  | + | 6.88 | 0.19 |
| $V^r$-$2_{16}$/$L_{929}$ | − | 4.34 | 2.78 |
|  | + | 6.79 | 0.28 |
| $V^r$-$2_{18}$/$L_{929}$ | − | 4.72 | 2.35 |
|  | + | 6.92 | 0.15 |
| $V^r$-$2_{19}$/$L_{929}$ | − | 4.32 | 2.75 |
|  | + | 6.89 | 0.18 |

$^a$The $log_{10}$ VSV yield is determined from the titer of infectious virus produced by each culture. The virus titer is first normalized on a PFU/$10^5$ cells basis and the $log_{10}$ of this number is then taken.
$^b$The $log_{10}$ VSV yield reduction is derived by first taking the $log_{10}$ of the sum of 50% of the virus yield, on a PFU/$10^5$ cells basis from individual cultures of each of the two cell types employed in the co-cultivation and then subtracting from this the $log_{10}$ of the virus yield again on a PFU/$10^5$ cells basis from co-cultivated cultures. Hence it is an expression of the ratio of the expected yield from the two cell types, assuming no transference of a molecule(s) capable of inducing an antiviral state, to the experimentally derived yield.

The above data demonstrate that there is significant production of interferon, which is secreted from the cell. Furthermore, the yields of virus in the presence of the hybridomas produced above is substantially below the virus yields of the parent mouse cells which were crossed with the $V^r$ phenotypic marker containing cell.

Following the procedure described above, normal cell lines and mutant cell lines were treated with different viruses, Newcastle disease virus (NDV) and blue tongue virus (BTV) as described above, and the units of interferon obtained determined. The following table indicates the results.

TABLE 3

| Cell Line | Interferon Pre-treatment | Inducing Virus | Interferon Yield IU/$10^7$ Cells |
|---|---|---|---|
| $L_{929}$ | No | NDV | $3 \times 10^4$ |
| $L_{929}$ | Yes | NDV | $10^3$ |
| $L_{929}$ | No | BTV | $<10$ |
| $L_{929}$ | Yes | BTV | $5 \times 10^4$ |
| 3T6 | No | NDV | $9 \times 10^2$ |
| 3T6 | Yes | NDV | $9 \times 10^2$ |
| 3T6 | No | BTV | $<10$ |
| 3T6 | Yes | BTV | $2 \times 10^2$ |
| 3T6 IF$^{sc}$ | No | NDV | $8 \times 10^2$ |
| 3T6 IF$^{sc}$ | No | BTV | $9 \times 10^5$ |
| Hybrid IF$^{sc}$ | No | NDV | $10^2$ |
| Hybrid IF$^{sc}$ | No | BTV | $5 \times 10^6$ | mRNA specific for interferon is induced by maintaining the hybrid cells in 30 ml of Eagle's Minimal Essential Medium (MEM) containing 10% fetal calf serum (FCS) in 150 mm tissue culture dishes. Th cells are infected with BTV at moi=1 in 3.0 ml of MEM containing 2% FCS for 45 minutes. The cells are then washed twice and 30 ml of MEM 2FCS added. At ten hours post infection, the cells are washed twice with ice-cold PBS and scrapped off with a rubber policemen into ice cold PBS containing 20 mg/ml cycloheximide and pelleted by centrifugation (1,000×g, 5 min). The cell pellet is then resuspended in a hypotonic buffer (10 mM tris-HCl, pH 7.6, 10 mM NaCl, 1.5 mM $MgCl_2$, 1 mM dithiothreitol), allowed to swell for 10 min and homogenized with 40 strokes in a Dounce homogenizer (tight pestle). A post-mitochondrial supernatant is then prepared by centrifugation (8,000×g, 10 min). Centrifugation of the supernatant (25,000×g, 20 min) then yields the "free" (supernatant) and "membrane" (pellet) fractions. Total RNA can then be extracted from either fraction with phenol-chloroform and poly(A)-rich RNA is then prepared by oligo (dT)-cellulose, chromatography.

Oocyte clusters are surgically removed from adult X. Laevis anesthesized by immersion in an ice-bath. Twenty to 30 oocytes are then injected with 125 nl of the RNA solution. Injected oocytes are incubated, ten oocytes/0.1 ml in Barth's medium for 48 hrs at 22° C. The injected oocytes are homogenized in incubation medium and the homogenate clarified by centrifugation (10,000×g, 5 min). An aliquot of the supernatant is assayed for interferon activity with an appropriate mammalian cell susceptible to interferon activity. See Abreu and Bancroft, Biochem. Biophys, Res. Comm. 82, 1300 (1978).

Substantially following the procedure described above, 3T6 $V^r$ B2 cells were crossed with human fibroblast (FS-4) (HFIF+). After combining $10^6$ cells of each parent under fusion conditions, followed by removal of the PEG solution and washing, the cultures are incubated for 18 hrs at 37° C., trypsinized and plated into 100 mm dishes in DME-10FCS. After about 24–28 hrs, the cells are trypsinized, counted with 0.05% trypan blue dye and plated out at between $10^3$ and $3 \times 10^3$ viable cells/100 mm dish in DME-10FCS.

The hybrids were selected by adding to the dish a selective medium of DME-10FCS-HAT-Oab; $10^{-4}$ M hypoxanthine, $5\times10^{-7}$ M aminopterin, $10^{-5}$ M thymidine and $10^{-6}$ M ouabain, and the mixture replaced at three day intervals. After identifying the colonies visually, the identified colonies are surrounded with stainless steel cloning cylinders and the cells and the cylinders trypsinized and plated into 35 mm dishes in the above described selective medium. The process is repeated at $10^3$ and $3\times10^3$ with plating and isolation for 40–50 generations.

The fusion of 3T6-V$^r$B2 with human leukocyte (HLeIF+) or lymphoblastoid (HLyIF+) cells is performed as follows. Mixed suspensions are prepared at about $2\times10^6$ of the mouse cells and $10^7$ of the human cells, the mixture washed $3\times$ with serum-free DME with centrifugation at 250 g for 5 min to separate the cells each time. The cells are then resuspended in 0.2 ml of 35% v/v PEG 6,000 in DME. The mixture is then centrifuged for 3 min at 500 g. After 8 min, 5 ml of DME is added, the mixture resuspended gently followed by centrifugation for 5 min at 250 g. After resuspending the cells in DME-10FCS the dispersion is plated into $2\times100$ mm dishes. In order to remove unattached cells after 6 hrs, the cultures are washed with DME-10FCS, followed by the addition of DME-10FCS containing $10^{-6}$ M ouabain. After one to two days, the cells are plated out at between $10^3$ and $3\times10^3$ cells/100 mm dish as above. The hybrids are selected in the same manner as described above using the selective medium in the same repetitive manner.

Following the procedure described above for fusion of the mouse cell IF$^{sc}$ with the human leukocyte or lymphoblastoid cells, an intraspecific cross may be employed by employing a mutagenized human lymphoblastoid cell which is IF$^{sc}$ with HFIF+, HGPRT−, Oab$^r$.

About $10^7$ cells of both the HLyIF$^{sc}$ and HFIF+ are mixed, and washed $3\times$ in serum free DME with centrifugation at 250 g for 5 mins. The cells are resuspended in 0.2 ml at 35% v/v PEG 6,000 in DME. After centrifugation for 3 min at 500 g, 8 min are allowed to elapse, followed by the addition of 5 ml DME, the cells resuspended gently and centrifuged for 5 min at 250 g. The cells are then resuspended DME-10FCS, plated into $2\times100$ mm dishes and after 6 hrs the cultures washed with DME-10FCS to remove the unattached cells followed by the addition of DME-10FCS containing $10^{-6}$ M ouabain. After one to two days, the cells are plated at $10^3$ plus $3\times10^3$ cells/100 mm dishes employing the selective medium DME-10FCS-HAT-Oab as described above. The mixture is then replaced at three day intervals for approximately 40 to 50 generations before being transferred to a medium without ouabain.

The various mutants and hybrids may be determined as follows. First, 16 mm duplicate cultures containing $1.2\times10^5$ cells in DME-10FCS are prepared of the cell line to be tested; human line, GM258; bovine line, MDBK; hybrid/GM258; and hybrid/MDBK. After one to two days, one of each duplicate is infected with VSV as described above. The virus containing medium is harvested at 10 hrs post infection from MDBK and at 18 hrs from GM258. The cultures at this time are examined for virus mediated cytopathic effects (CPE). The MDBK and GM258 will show CPE at 10 hrs and 18 hrs. respectively. The hybrids having V$^r$ phenotype should show little or no CPE. The hybrid/GM258 without CPE will indicate either HLeIF$^{sc}$ or HFIF$^{sc}$ hybrids, while the MDBK lacking CPE will indicate the presence of the hybrid HLeIF$^{sc}$. The virus titers are obtained as described above by standard plaque assay on BHK$_{21}$ cells for GM258, MDBK and hybrid and hybrid mixes that are visually identified as having IF$^{sc}$ phenotype.

Isolation of hybrids over producing human interferon (IF)

Cells to be tested are prepared as 35 mm cultures in triplicate in F15-10FCS at $10^6$ cells/well. After 18 to 24 hrs, the cultures are washed $2\times$ with warm serum-free F15 medium, followed by infecting duplicate cultures with 0.4 ml F15 containing $1.5\times10^6$ PFU blue tongue virus (BTV). After 45 min for virus adsorption, the culture is washed $3\times$ with F15-2FCS and incubated for 24 hrs with 3 ml F15-2FCS. The cells are then harvested from each culture chilled to 0° C. in an ice-bath and the pH reduced to about 2 by dropwise addition of ice-cold 1 N HCl with intermittent stirring. The mixture is then allowed to stand on ice for 1–2 hrs. After centrifugation at 2,000 rpm for 15 min at 4° C., the supernatant is carefully removed and assayed for HLeIF and HFIF using GM258 or MDBK cells and VSV as the challenge virus as described above.

Hybrid colonies which produce in excess of $10^6$ IU of interferon/$10^7$ cells are chosen for further study. The hybrids that overproduce human IF mRNA are identified as follows. Into roller bottles are injected $10^8$ cells and grown in DMF-10FCS to confluency. After washing the cultures twice with serum-free F15, the cultures are infected with BTV at MOI=1 for 45 min. The cultures are then washed with serum free F15, followed by the addition of 50 ml F15-2FCS to each roller bottle and the mixture incubated for 10 hrs.

After washing the cells twice with ice-cold phosphate buffered saline (PBS) the cells are removed by scrapping in the cold followed by centrifugation for 5 min at $1,000\times g$ at 0° C. The cells are then resuspended in 10 cell pellet volumes of RSB (10 mM tris-HCl, pH 8.5; 10 mM NaCl; 1.5 mM MgCl$_2$). The cells are allowed to swell for 10 min on ice followed by rupturing with 15–20 strokes by Dounce homogenization, keeping the system on ice during the process.

The nuclei are removed by centifugation, 10 min at 3,000 g, and the supernatant carefully isolated. After centrifuging the supernatant for 20 min at 22,000 g the pellet which contains the membrane bound polysomes is isolated as the source of IF mRNA. The pellet is resuspended in ice-cold aqueous 10 mM Hepes, pH 5; 0.05 mM NaOAc; 0.6% w/v SDS (sodium dodecyl sulfate). The polysomes are deproteinized by repeated extraction with phenol and chloroform. RNA is precipitated by the addition of two volumes of ethanol and allowed to stand at −20° C. overnight. The RNA is collected by centrifugation at 12,000 g at −20° C. for 20 min. The RNA pellet is washed twice with 70% ethanol and is dissolved in 0.5 M NaCl, 0.001 M EDTA, 0.01 M tris-HCl (pH 7.2), 0.25% SDS.

The above solution at a concentration of about $100 A_{260}$ units is applied to a 2 ml (about 0.5 g dry weight) oligo dT-cellulose column previously washed with the buffer. The nonabsorbed material is eluted by continued washing with the application buffer. The material retained by the column is eluted with buffers of reduced ionic strength. The elution buffer contains 0.01 M tris-HCl (pH 7.2), 0.001 M EDTA, 0.25% SDS. The material eluted in this way is immediately precipitated by the addition of sodium acetate and two volumes of ethanol as described above.

After centrifugation at 10,000 g for 30 min the resulting mRNA is redissolved in 0.5 ml of 0.01 M tris-HCl, (pH 7.4); 0.01 M EDTA; 0.1 M NaCl; 0.2% w/v SDS and the mixture heated at 60° C. for 3 min followed by quick cooling in an ice-bath. The RNA solution is layered onto a sucrose gradient, 15–30%, in the same buffer solution and centrifuged for 20 hrs at 22,000 g at 4° C. The fractions are collected from the gradient by monitoring the UV absorbance at 260 nm.

The mRNA is precipitated from each fraction by sodium acetate-ethanol treatment and centrifugation as described above.

The mRNA fractions are then assayed for IF mRNA activity using microinjection into frog oocytes. Oocyte clusters are surgically removed from adult *X. laevis* anesthetized by immersion in an ice bath. Twenty to thirty oocytes are each injected with 100–125 nl of RNA solutions containing about 0.4 ng of RNA/nl, the injected oocytes are then incubated, ten oocytes/0.1 ml in Barth's medium for 48 hrs at 22° C. After homogenizing the injected oocytes in the incubation medium the homogenate is clarified by centrifugation at 10,000 g, 5 min, and an aliquot of the supernatant is assayed for interferon activity in human GM258 cells and the results expressed as units/ml in the supernatant. The interferon is measured by employing the reduction in VSV-induced cytopathic effects on the cells as described above.

For further study, the hybrid colonies that produce 50–100 fold excess IF mRNA compared with super induced FS-4 cell cultures are chosen. The preparation of IF cDNA from IF mRNA is as follows. The IF mRNA is prepared from appropriate hybrid cells using $5 \times 10^8$–$10^9$ cells for preparation accumulating mRNA until approximately 0.5 mg is available. The technique described above can be employed or, in addition, polyacrylamide gel electrophoresis with formamide may be employed, following the sucrose gradient step according to Piender, et al. (1974) Biochemistry 13:5373–5378.

Preparation of cDNA from IF mRNA cDNA is prepared in a total volume of 10 µl in micro test tubes. A standard reaction mixture consists of: 50 mM tris-HCl, pH 8.3, at 42° C., 10 mM MgCl$_2$, 30 mM β-mercaptoethanol, 140 mM KCl, 100 µg/ml of oligo dT$_{12-18}$, 500 µM concentration of each deoxynucleotide triphosphate, five to 50 µg of RNA/ml and AM virus reverse transcriptase at ten units/µg of RNA. The amounts of enzyme and oligo-(dT) are saturated. The mRNA is added to a final concentration of 10 to 40 µg/ml. After being assembled on ice, mixed and centrifuged briefly, reactions are incubated at 42° C. for 60 min. The reactions are stopped by chilling on ice and briefly centrifuging. Tubes are then placed in a boiling water bath for 3 min to separate mRNA-first strand hybrids and plunged immediately into an ice-water bath. After a short centifugation to pelletize denatured protein, the tubes are returned to ice.

The cold, boiled reverse transcriptase reaction mixture is added to an equal volume of cold DNA polymerase I reaction mixture (200 mM Hepes, pH 6.9 and 500 µM concentration of each deoxynucleoside triphosphate). The mixture is then incubated for 2 hrs at 15°.

Second strand synthesis is stopped by chilling on ice and by the addition of 100 µl of a deactivation mixture containing 10 mM dGTP, 0.1% SDS and 20 to 50 µg of *E. coli* tRNA. The reaction mixture is then extracted at room temperature with approximately 0.4 ml chloroform in the organic phase and interphase reextracted with 100 to 200 µl of 20 mM NaCl. Pooled aqueous phases of about 200–400 µl volume are passed over 6 to 7 ml bed volume Sephadex G-150 columns formed into 5 ml plastic pipettes plugged with siliconized glass wool and equilibrated in 20 mM NaCl or water. Approximately 0.6 ml fractions are collected into sterile 5 ml polypropylene tubes.

Column fractions containing the ds cDNA are adjusted to 40 mM NaOAc pH 4.5, 300 mM NaCl, 3 mM Zn(OAc)$_2$ and then treated with *Aspergillus oryzae* Sl nuclease (5U/ml) as described by Wickens et al., J. Biol. Chem 253, 2483 (1978). The digestion was carried out at 37° for 60 min and stopped by the addition of EDTA to 10 mM. After extraction with phenol and ether (as previously described) followed by adjusting to 0.3 M NaCl and precipitation with ethanol, approximately 1.0 µg ds cDNA is obtained. Aliquots of second strand product after Sl nuclease treatment are examined on a 1.5% agarose gel under alkaline conditions as described by McDonnell et al., *J. Mol. Biol.*, 110, 119 (1977). Terminal addition of dCTP to the ds cDNA by terminal deoxynucleotidyl transferase (TdT, Chang and Bollum, *J. Biol. Chem.* 246, 909 (1971)) is carried out by a modification of the Co$^{++}$ procedure (Roychoudhury et al., *Nuc. Acids Res.*, 3, 101 (1976). The reaction is performed in 500 µl containing 140 cacodylic acid, 30 mM Tris base, 110 mM KOH (final pH 7.6), 0.1 mM dithiothreitol, 150 µl dCTP (adjusted to 8 Ci/mm with $^3$H-dCTP), 1 mM CoCl$_2$ (added to prewarmed reaction mix prior to enzyme addition), approximately 1.0 µg ds cDNA and 0.5 µl TdT ($2.3 \times 10^5$ units/ml). The reaction is allowed to proceed at 37° for 10 minutes before being cooled and sampled to determine incorporation. Approximately 30 dC residues are added per 3' terminus. The reaction is stopped (EDTA to 10 mM), extracted, desalted and precipitated with ethanol as above. Aliquots (a) second strand product after Sl nuclease treatment and (b) dC-tailed ds cDNA are analyzed on a 1.7% agarose gel in Tris-acetate-NaCl. The dC-tailed ds cDNA is then preparatively electrophoresed on a similar gel and the desired base pair region (~200–500 base pairs) cut out of the gel and electrophoretically eluted into a dialysis bag (see McDonnell et al., supra.). The eluted material is extracted as above, concentrated by lyophilization and precipitated with ethanol. After centrifugation, the dC-tailed ds cDNA (approximately 80 ng) is redissolved in 10 mM Tris-HCl, pH 7.4, 0.25 mM EDTA, 100 mM NaCl (annealing buffer).

pBR322 plasmid DNA, isolated as described (Kuperstock and Helinski, *Biochem. Biophys. Res. Commun.*, 54, 1451 (1973)) is digested with a 1.5 fold excess of PstI endonuclease under conditions suggested by the vendor (New England Biolabs) and the linear plasmid DNA is cut out and eluted as discribed above from a 0.7% agarose gel in TBE (Sharp and Sambrook, *Biochemistry*, 12, 3055 (1974). The plasmid DNA is 'tailed' with dG residues following the procedures described above. Approximately 15–20 dG residues are added per 3' terminus. Following extraction with phenol and ethanol as previously described, the dG-tailed vector is passed over a Sephade G-50 file column (0.5×7 cm) in annealing buffer and the void volume is collected. Equimolar amounts of dC-tailed ds cDNA and dG-tailed vector DNA are allowed to anneal essentially as described in Sanger and Coulson, FEBS Lett., 87, 107 (1978), except that the vector concentration is kept at 75 ng/ml in the annealing reaction. Circularization is monitored by electron microscopy and is typically about 20–40%. This annealed DNA is used directly for transformation into a compatible microorganism e.g. $\chi$1776 or $\chi$2282.

Transformation and identification of clones

The transformation of $\chi$1776 is performed by growing $\chi$1776 in L broth supplemented with 10 μg/ml of diaminopimelic acid (DAP) and 40 μg/ml thymidine to $A_{590}$ of 0.5. Cells (200 ml) are sedimented by centifugation at 3,000 rpm and resuspended by swirling in 0.1 volume of cold buffer containing 70 mM $MnCl_2$, 40 mM sodium acetate, pH 5.6, 30 mM $CaCl_2$ and kept on ice for 20 min. The cells are repelleted and resuspended in 1/30 of the original volume in the same buffer. The annealed DNA preparation (2 ml) is added to the cells and aliquots of this mixture (0.3 ml) are placed in sterile tubes and incubated on ice for 60 min. The cells are then placed at 37° for 2 min followed by adding 0.7 ml broth to each tube and incubating at 37° for 15 min. Nitrocellulose filters (previously boiled to remove detergents) overlaying agar plates containing 15 μg/ml tetracycline are streaked with 200 μl of the cells and the plates incubated at 37° for 48 hrs. The nitrocellulose filters containing the transformants are removed from the agar and placed on a layer of sterile Whatman filter paper, a new sterile filter placed on the filter containing the colonies and pressure applied with a sterile velvet cloth and a duplicate block. A sterile needle is used to key the filters. The second filter is placed on a new agar plate and incubated at 37° for 48 hrs. The colonies on the first filter are screened by the Grunstein-Hogness technique (Grunstein and Hogness (1975) PNAS USA 72,3961–3965), using as the probe an 80 nucleotide long fragment produced by HaeIII digestion of high specific activity cDNA.

The clones are further screened by combining the transformants with virus suspectible cells as described above, and employing a viral infection at a MOI of about seven, in the presence and absence of anti-interferon and determining the viral yield. The substantial decrease of viral yield in the absence of anti-interferon as compared to the presence of anti-interferon, indicates a transformant capable of expressing the interferon gene.

In order to isolate the interferon, stationary phase cultures of the microorganism are grown in minimal medium, washed with isotonic saline, and suspended in 50 mM potassium phosphate buffer, pH 7, containing 10 mM benzamidine and 10 mM phenylmethylsulfonylfloride (three volumes buffer to one volume cells). The suspension is centrifuged at 10,000 rpm and the cell free supernatant isolated and the interferon obtained by conventional means, such as gel electrophoresis, density gradient centrifugation, HPLC, affinity chromatography, or the like.

In accordance with the subject invention, various mammalian interferons can be produced to provide interferon in significant amounts in highly purified form, substantially free of contaminating proteins, which may have a antigenicity for a mammalian species. The method is predicated on the ability to obtain mRNA specific for interferon for a particular species, which can then be employed in recombinant DNA technology to provide for continued production of the species specific interferon employing a microorganism. Thus, prokaryotc and eukaryotc microorganisms may be employed for the continued production of mammalian interferon, where the interferon can be obtained in good yield, high concentration, and substantially free of contaminating proteins. The interferon which is obtained is obtained free of saccharidic substituents, but retains at least a substantial proportion of its activity in inducing an antiviral state in mammalian cells.

Although the foregoing invention has been described in some detail by way of illustration and example for purposes of clarity of understanding, it will be obvious that certain changes and modifications may be practiced within the scope of the appended claims.

What is claimed is:

1. A method for producing mRNA specific for mammalian interferon in amounts sufficient to be useful for formation of recombinant DNA capable of transformation of microorganisms to form transformants, which are capable of replication of said recombinant DNA and expression of ds cDNA derived from said mRNA, said method comprising fusing intra- or inter-specifically a mammalian cell semi-constitutive for interferon with a mammalian cell which is wild type for interferon to produce hybrid cells; inducing the hybrid cells to overproduce mRNA specific for interferon, and isolating the overproduced mRNA.

2. A method according to claim 1, wherein said cells are murine cells.

3. A method according to claim 1, wherein at least one of said cells is a human cell.

4. A method according to any of claims 1 to 3, wherein said inducing is with blue tongue virus.

5. A method for producing mRNA specific for murine interferon which comprises:

fusing a 3T6 murine cell semiconstitutive for interferon with a murine cell having at least one phenotypic property and wild type for interferon to produce a hybrid cell;

isolating and cloning said hybrid cells by means of said phenotypic property;

inducing overproduction of mRNA specific for interferon by adding virus to said cells; and isolating said mRNA specific for murine interferon.

* * * * *